(12) United States Patent
Johannaber (10) Patent No.: US 11,491,030 B2
(45) Date of Patent: *Nov. 8, 2022

(54) SHOULDER ARTHROPLASTY TRIAL DEVICE

(71) Applicant: Zimmer, Inc., Warsaw, IN (US)

(72) Inventor: Kenneth D. Johannaber, Reno, NV (US)

(73) Assignee: Zimmer, Inc., Warsaw, IN (US)

( * ) Notice: Subject to any disclaimer, the term of this patent is extended or adjusted under 35 U.S.C. 154(b) by 452 days.

This patent is subject to a terminal disclaimer.

(21) Appl. No.: 16/703,327

(22) Filed: Dec. 4, 2019

(65) Prior Publication Data
US 2020/0100911 A1    Apr. 2, 2020

Related U.S. Application Data

(63) Continuation of application No. 15/801,066, filed on Nov. 1, 2017, now Pat. No. 10,524,934.

(51) Int. Cl.
*A61F 2/46* (2006.01)
*A61F 2/40* (2006.01)
(Continued)

(52) U.S. Cl.
CPC .......... *A61F 2/468* (2013.01); *A61B 17/1684* (2013.01); *A61F 2/4014* (2013.01); *A61F 2/4081* (2013.01); *A61F 2/4612* (2013.01); *A61F 2/4657* (2013.01); *A61F 2/4684* (2013.01); *A61B 5/4576* (2013.01); *A61B 2017/00022* (2013.01); *A61B 2017/00115* (2013.01); *A61B 2017/00199* (2013.01); *A61B 2017/00716* (2013.01); *A61B 2090/064* (2016.02); *A61F 2/40* (2013.01); *A61F 2/4603* (2013.01); *A61F 2002/4666* (2013.01)

(58) Field of Classification Search
CPC ...... A61F 2/468; A61F 2/4684; A61F 2/4603; A61F 2/4612; A61F 2002/4666; A61F 2/4605; A61F 2/461; A61F 2/4618; A61B 2017/00022; A61B 2017/00199
See application file for complete search history.

(56) References Cited

U.S. PATENT DOCUMENTS 5,470,354 A * 11/1995 Hershberger ......... A61F 2/4684
600/595
7,578,821 B2 * 8/2009 Fisher ................... A61F 2/4684
606/88

(Continued)

OTHER PUBLICATIONS

"U.S. Appl. No. 15/801,066, Corrected Notice of Allowability dated Nov. 7, 2019", 4 pgs.

(Continued)

*Primary Examiner* — Alvin J Stewart
(74) *Attorney, Agent, or Firm* — Schwegman Lundberg & Woessner, P.A.

(57) ABSTRACT

A arthroplasty trial tool for a human shoulder can include a handle, a first sensor, and a user interface. The handle can include a first end and a second end opposite the first end. The first sensor can produce a first sensor signal as a function of a sensed shoulder condition. The user interface can be configured to display a first value as a function of the first sensor signal.

20 Claims, 4 Drawing Sheets

Related U.S. Application Data (60) Provisional application No. 62/440,583, filed on Dec. 30, 2016.

(51) Int. Cl.
*A61B 17/16* (2006.01)
*A61B 5/00* (2006.01)
*A61B 17/00* (2006.01)
*A61B 90/00* (2016.01)

(56) References Cited

U.S. PATENT DOCUMENTS

| | | | |
|---|---|---|---|
| 8,597,210 B2 | 12/2013 | Sherman et al. | |
| 8,721,568 B2 | 5/2014 | Rock et al. | |
| 8,758,355 B2* | 6/2014 | Fisher | A61F 2/3859 606/88 |
| 8,858,623 B2 | 10/2014 | Miller et al. | |
| 8,926,695 B2 | 1/2015 | Gross et al. | |
| D725,774 S * | 3/2015 | Lubensky | D24/140 |
| 8,973,281 B1* | 3/2015 | Fiquette | G01B 3/002 33/501.45 |
| 9,265,608 B2 | 2/2016 | Miller et al. | |
| 9,414,940 B2* | 8/2016 | Stein | A61F 2/4657 |
| 9,462,967 B2* | 10/2016 | Boggs | A61B 5/1121 |
| 9,775,709 B2 | 10/2017 | Miller et al. | |
| 10,206,792 B2* | 2/2019 | Sherman | A61F 2/4657 |
| 10,524,934 B2* | 1/2020 | Johannaber | A61B 17/1684 |
| 10,980,647 B2* | 4/2021 | Patel | A61B 5/4585 |
| 11,298,246 B1* | 4/2022 | Cole | G16H 40/20 |
| 2005/0203541 A1* | 9/2005 | Steffensmeier | A61B 90/06 606/102 |
| 2006/0184067 A1* | 8/2006 | Clark | G01L 1/205 600/587 |
| 2010/0161047 A1 | 6/2010 | Cabiri | |
| 2010/0217156 A1* | 8/2010 | Fisher | A61F 2/4657 600/587 |
| 2010/0331734 A1 | 12/2010 | Stein | |
| 2010/0331737 A1 | 12/2010 | Stein et al. | |
| 2010/0332152 A1 | 12/2010 | Stein | |
| 2011/0106247 A1 | 5/2011 | Miller et al. | |
| 2011/0224785 A1 | 9/2011 | Hacohen | |
| 2011/0319755 A1 | 12/2011 | Stein et al. | |
| 2012/0022639 A1 | 1/2012 | Hacohen et al. | |
| 2012/0022640 A1 | 1/2012 | Gross et al. | |
| 2012/0136436 A1 | 5/2012 | Cabiri et al. | |
| 2012/0152017 A1* | 6/2012 | Stein | A61B 5/4528 73/379.01 |
| 2012/0283757 A1 | 11/2012 | Miller et al. | |
| 2013/0046373 A1 | 2/2013 | Cartledge et al. | |
| 2013/0079787 A1* | 3/2013 | Spencer Jones | A61F 2/4684 606/96 |
| 2013/0261502 A1* | 10/2013 | Sherman | A61F 2/4657 600/587 |
| 2013/0310841 A1* | 11/2013 | Fitz | A61B 5/1072 606/102 |
| 2013/0331850 A1* | 12/2013 | Bojarski | A61F 2/4657 606/102 |
| 2014/0296962 A1 | 10/2014 | Cartledge et al. | |
| 2015/0112432 A1 | 4/2015 | Reich et al. | |
| 2016/0310297 A1* | 10/2016 | Anes | A61F 2/38 |
| 2016/0361168 A1 | 12/2016 | Gross et al. | |
| 2016/0361169 A1 | 12/2016 | Gross et al. | |
| 2017/0000609 A1 | 1/2017 | Gross et al. | |
| 2017/0196507 A1* | 7/2017 | Singh | A61B 5/4528 |
| 2018/0185166 A1 | 7/2018 | Johannaber | |
| 2018/0214283 A1* | 8/2018 | Johannaber | A61F 2/4657 |
| 2020/0107945 A1* | 4/2020 | Trousdale | A61B 5/4576 |
| 2020/0113714 A1* | 4/2020 | Patel | A61F 2/4684 |
| 2020/0352556 A1* | 11/2020 | Walker | A61B 17/025 |
| 2022/0096248 A1* | 3/2022 | Dressler | A61B 90/06 |

OTHER PUBLICATIONS

"U.S. Appl. No. 15/801,066, Non Final Office Action dated Mar. 1, 2019", 7 pgs.

"U.S. Appl. No. 15/801,066, Notice of Allowance dated Sep. 4, 2019", 8 pgs.

"U.S. Appl. No. 15/801,066, Response filed Feb. 14, 19 to Restriction Requirement dated Dec. 27, 2018", 7 pgs.

"U.S. Appl. No. 15/801,066, Response filed May 29, 19 to Non-Final Office Action dated Mar. 1, 2019", 10 pgs.

"U.S. Appl. No. 15/801,066, Restriction Requirement dated Dec. 27, 2018", 5 pgs.

* cited by examiner

SHOULDER ARTHROPLASTY TRIAL DEVICE

CLAIM OF PRIORITY

This application is a continuation of U.S. patent application Ser. No. 15/801,066, filed on Nov. 1, 2017, which claims the benefit of U.S. Provisional Patent Application Ser. No. 62/440,583, filed on Dec. 30, 2016, the benefit of priority of each of which is claimed hereby, and each of which is incorporated by reference herein in its entirety.

FIELD

The present subject matter relates to orthopedic procedures and, more particularly, to assemblies and systems that can aid in shoulder procedures.

BACKGROUND

The shoulder joint is a complex joint with the scapula, clavicle and the humerus all coming together to enable a wide range of movement, at least in a properly functioning joint. In a properly functioning shoulder joint the head of the humerus fits into a shallow socket in the scapula, typically referred to as the glenoid. Articulation of the shoulder joint involves movement of the humeral head in the glenoid, with the structure of the mating surfaces and surrounding tissues providing a wide range of motion.

The shoulder joint can undergo degenerative changes caused by various issues, such as rheumatoid arthritis, osteoarthritis, rotator cuff arthroplasty, vascular necrosis, or bone fracture. When severe joint damage occurs and no other means of treatment is found to be effective, a total, partial, or reverse shoulder replacement or reconstruction may be necessary. Total shoulder replacements can involve a humeral prosthetic, including a stem and a head portion used to replace the natural humeral head. Total shoulder replacements will also typically involve resurfacing of the glenoid with a prosthetic implant. The glenoid implant generally will include an articulating cup shaped to receive the prosthetic humeral head. A reversal shoulder replacement (arthroplasty) involves a different set of humeral and glenoid replacement prosthetics. In a reverse shoulder the humeral component includes a cup shaped articular surface attached to a stem implanted into the humerus, while a spherical glenoid component is used to provide an articular surface for the humeral cup.

OVERVIEW

During shoulder arthroplasty surgery, the components of the prosthesis are matched with the bio-kinematics of the patient in an effort to maintain or restore a natural range of motion of a healthy shoulder joint. Patient specific instrumentation can assist a surgeon in planning and implementing a shoulder arthroplasty to restore natural bio-kinematics. However, even with the multitude of advances in prosthetic components and patient specific instrumentation, restoring a full range of motion can remain difficult, especially for a surgeon who does not regularly perform shoulder replacements.

Even current surgical standards are often vague, providing guidance such as joint tension should be 50/50 laxity or the joint should be "stable" throughout the range of motion. It is common for the current surgical standards to use un-quantified subjective measures, such as if the fit is "too tight," soft tissue releases may be performed. Without significant experience, such guidance is of little practical use in ensuring successful outcomes.

The systems, devices, methods, and instruments discussed herein can provide quantitative measurements to assist surgeons in determining whether trial prosthetic devices may provide a patient with desirable outcomes. Providing quantitative values representative of joint tension and/or range of motion, can allow for development of definitive standards of care that routinely result in successful outcomes. Quantitative measurements of certain parameters critical to providing a functional joint also allow for surgeons to knowingly account to patient specific issues, rather than the present vague "feel" that only the most experienced surgeons are likely to use successfully.

While the above discusses issues and procedures specific to shoulder replacement procedures, discussion of the following systems, devices, methods, and instruments is also applicable for use in other joint replacement procedures, such as total hip arthroplasty (THA) or total knee arthroplasty (TKA).

To further illustrate the apparatuses and systems disclosed herein, the following non-limiting examples are provided:

Example 1 is an arthroplasty trial tool for a human shoulder comprising: a handle comprising a first end and a second end opposite the first end, the first end comprising: a first sensor configured to produce a first sensor signal based on a sensed condition of the human shoulder when the first end engages a humeral-glenoid interface of the human shoulder; and a user interface disposed on the handle between the first end and the second end, the user interface configured to display a first value indicative of stability of the shoulder based on the first sensor signal.

In Example 2, the subject matter of Example 1 optionally includes the second end further comprising: a second sensor configured to produce a second sensor signal based on a second sensed condition of the human shoulder when the second end engages the humeral-glenoid interface, the second sensor signal indicative of stability of the shoulder.

In Example 3, the subject matter of Example 2 optionally includes wherein the user interface is configured to display a second value based on the second sensor signal.

In Example 4, the subject matter of any one or more of Examples 2-3 optionally include wherein at least one of the first sensor and the second sensor comprises a force sensor.

In Example 5, the subject matter of Example 4 optionally includes wherein the user interface is configured to display a force value based on at least one of the first sensor signal and the second sensor signal, wherein the force value is indicative of stability of the humeral-glenoid interface.

In Example 6, the subject matter of any one or more of Examples 1-5 optionally include the user interface further comprising: a light emitting diode (LED) display configured to display a numerical value representing at least one of the first sensor signal and the second sensor signal.

In Example 7, the subject matter of Example 6 optionally includes wherein the LED display is configured to display a first numerical value representing the first sensor signal and a second numerical value representing the second sensor signal.

In Example 8, the subject matter of any one or more of Examples 1-7 optionally include wherein the first end comprises a first size that is different from a second size of the second end.

In Example 9, the subject matter of any one or more of Examples 1-8 optionally include the first end further comprising: a convex side engageable with a concave portion of the humeral-glenoid interface; and a concave side engageable with a convex portion of the humeral-glenoid interface.

In Example 10, the subject matter of any one or more of Examples 1-9 optionally include wherein the humeral-glenoid interface comprises one or more trial components associated with a shoulder replacement prosthesis.

Example 11 is an arthroplasty trial system for a human shoulder, the trial system comprising: a set of implants comprising a humeral implant and a glenoid implant; a trial tool comprising: a body comprising a first end and a second end; a spoon coupled to the first end, the spoon engageable with the set of implants, the spoon comprising: a sensor to produce a sensor signal based on a condition of the set of implants when the spoon engages the set of implants; and a user interface located on the body and configured to, based on the first sensor signal, display a value indicative of the condition of the set of implants.

In Example 12, the subject matter of Example 11 optionally includes wherein the value displayed is a force value indicative of stability of the human shoulder including the set of implants.

In Example 13, the subject matter of any one or more of Examples 11-12 optionally include a second spoon coupled to the second end of the body, the second spoon including a second sensor configured to produce a second sensor signal based on a second condition of the set of implants when the second spoon engages the set of implants.

In Example 14, the subject matter of Example 13 optionally includes wherein the user interface is configured to display a second value based on the second sensor signal, the displayed second value indicative of stability of the human shoulder including the set of implants.

In Example 15, the subject matter of any one or more of Examples 11-14 optionally include wherein the first spoon comprises a first size that is different from a second size of the second spoon.

In Example 16, the subject matter of any one or more of Examples 11-15 optionally include a second set of implants comprising a second humeral implant and a second glenoid implant, the second humeral implant having a second humeral implant size that is different than a size of the humeral implant.

In Example 17, the subject matter of Example 16 optionally includes wherein the first spoon is configured to engage the second set of implants to produce a second sensor signal based on a second condition of the second set of implants.

Example 18 is a method of evaluating trial components, comprising: inserting a first end of a trial tool into a shoulder of patient adjacent to a first trial component; producing a first sensor signal based on a condition of the first trial component installed on the shoulder using the trial tool; producing, based on the first sensor signal, a display on the trial tool representing the condition of the first trial component indicative of stability of the shoulder; and selecting the first trial component based on the display.

In Example 19, the subject matter of Example 18 optionally includes securing the first trial component to a glenoid of the shoulder of the patient; securing a second trial component to a humerus of the shoulder of the patient; and producing a first sensor signal based on a condition of the first trial component and the second trial component using a first end of the trial tool; and producing, based on the first sensor signal, a display representing the condition of the first trial component and the second trial component using a second end of the trial tool.

In Example 20, the subject matter of any one or more of Examples 18-19 optionally include adjusting the first trial component based on the display, wherein adjusting the first trial component comprises one or more of moving the first trial component, rotating the first trial component, moving the second trial component, rotating the second trial component, inserting a new first trial component, and inserting a new second trial component.

In Example 21, the device, assembly, or method of any one of or any combination of Examples 1-20 is optionally configured such that all elements or options recited are available to use or select from.

These and other examples and features of the present apparatuses and systems will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices and systems for shoulder replacement procedures, such as a reverse shoulder arthroplasty and total or an anatomical shoulder arthroplasty. Such procedures can include the use of trial components, which are installable prior to installation of the permanent prosthetic components. Trial components can be used to determine fit of the joint, such as the stability of the joint, and can be used to select appropriately sized permanent prosthetic components.

Figure 1:
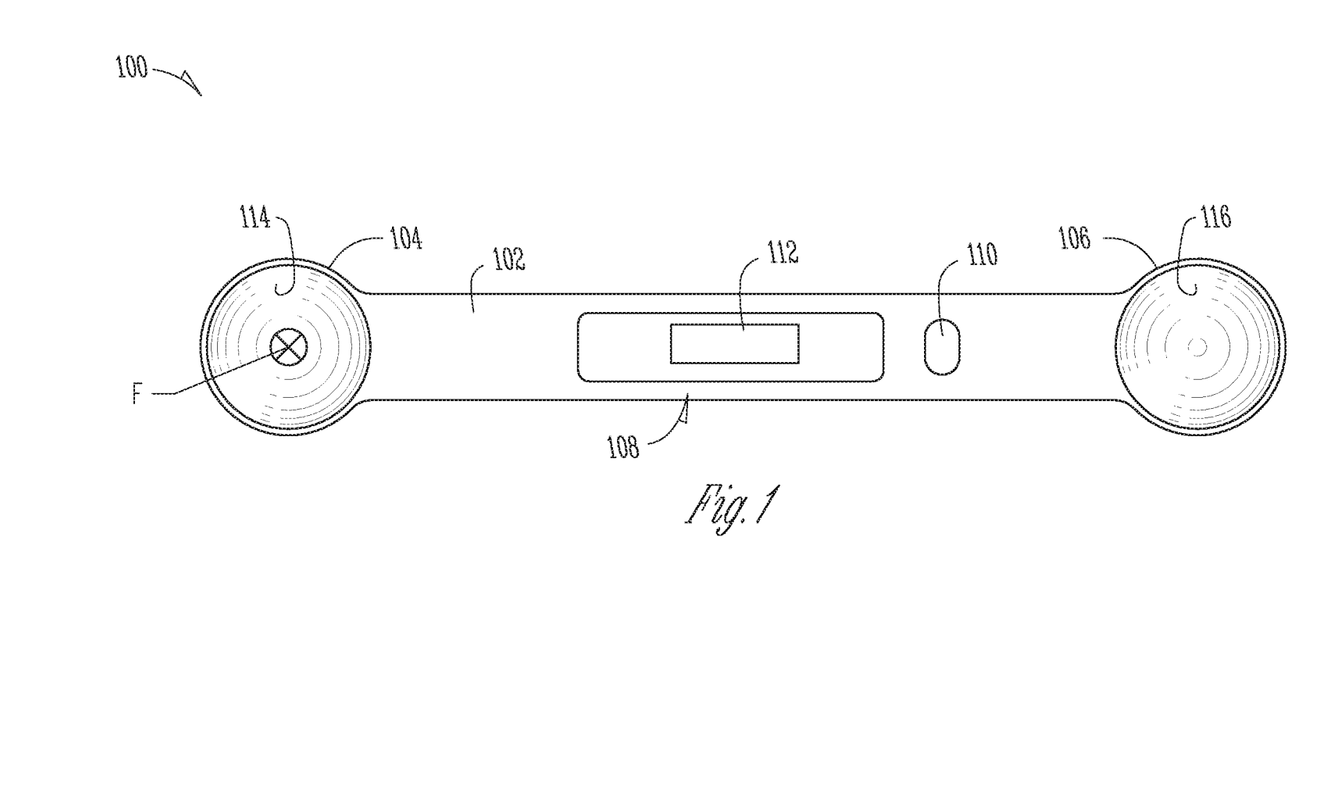
FIG. 1 illustrates a perspective view of a trial spoon in accordance with one example of the present disclosure.

FIG. 1 illustrates a perspective view of trial spoon 100, which can include handle 102, first end 104, second end 106, and user interface 108. User interface 108 can include button 110 and display 112. First end 104 can include spoon 114 and second end 106 can include spoon 116. Also shown in FIG. 1 are orientation indicators Left and Right and force F (shown as into the page).

Handle 102 can be an elongate body comprised of metal, plastic, and the like. Handle 102 can be coupled to first end 104 at a left end of handle 102. First end 104 and second end 106 can be comprised of plastic, metal, and the like. First end can 104 can include spoon 114, in some examples. Spoon 114 can have a spoon shape, such as mated concave and convex portions. Similarly, handle 102 can be coupled to second end 106 at a right end of handle 102. Second end can 106 can include spoon 116, in some examples. Spoon 116 can have a spoon shape, such as mated concave and convex portions. First end 104 and second end 106 can each include a sensor configured to produce a sensor signal as a function of a condition of their respective spoons, such as a force applied to the spoon, as discussed further below.

User interface 108 can include (in addition to button 110 and display 112), a circuit board, controller, and other electronics required to display values on display 112, as discussed further below. Button 110 can be a switch or other electrical component configured to receive user input. Button 110 can be electrically connected to user interface 108. Also, sensors within each of spoons 114 and 116 can be connected to user interface 108.

Display 112 can be a screen, such as a light emitting diode (LED) display, liquid crystal display (LCD), and the like. Display 112 can be electrically connected to other components of user interface 108, such as a controller and/or circuit board, as discussed further below. Display 112 can also be connected to sensors within spoons 114 and 116, and display 112 can be connected to button 110.

Further examples of operations and functions of spoon 100 are discussed in FIGS. 2-4 below.

Figure 2:
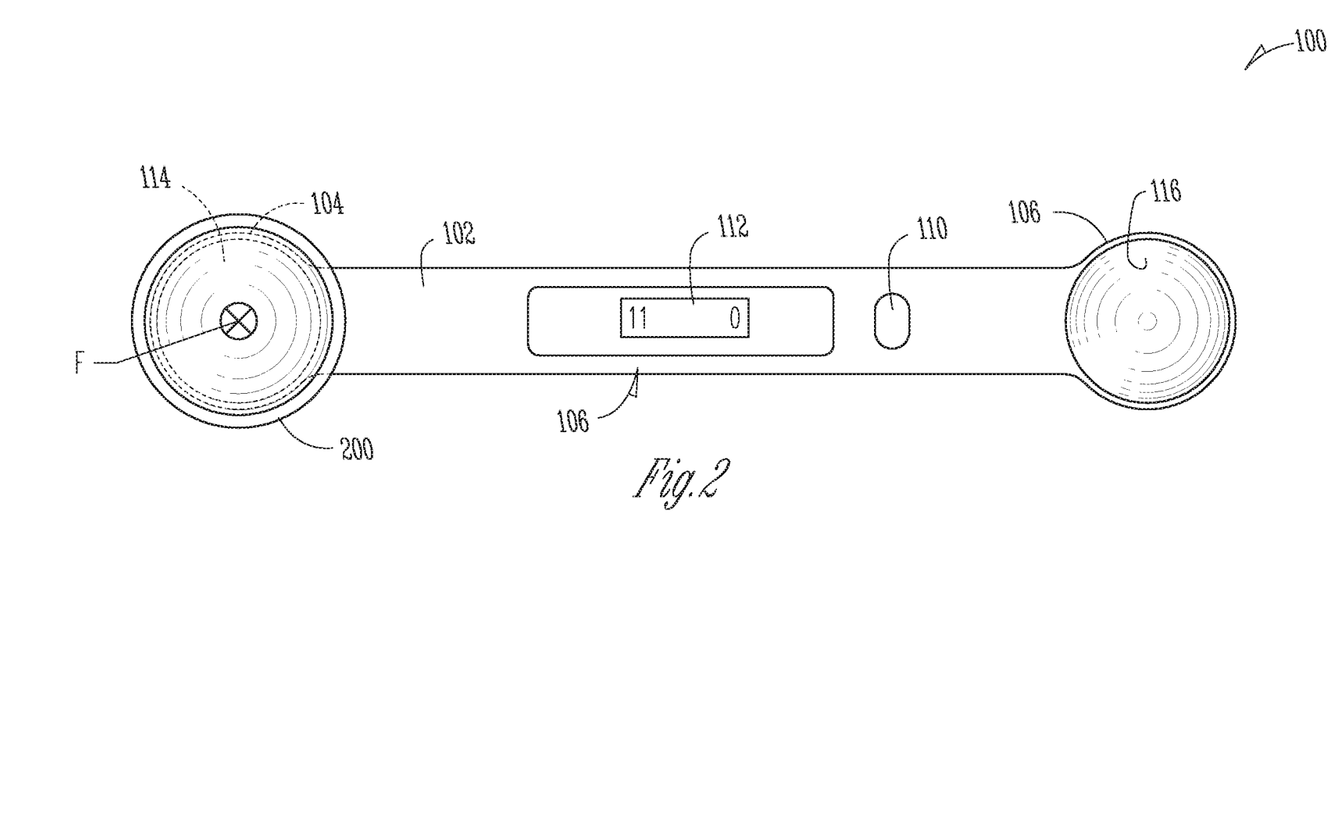
FIG. 2 illustrates a partial perspective view of a trial spoon in accordance with one example of the present disclosure.

FIG. 2 illustrates a partial perspective view of trial spoon 100, which can include handle 102, first end 104, second end 106 (not shown), and user interface 108. User interface 108 can include button 110 and display 112. First end 104 can include spoon 114 and second end 106 (not shown) can include spoon 116 (not shown). Also shown in FIG. 2 are trial components 200, orientation indicators Left and Right, and force F (shown is into the page).

The components of trial spoon 100 shown in FIG. 2 are consistent with those shown in FIG. 1; however, FIG. 2 further shows how trial spoon 100 can be operated in some examples.

Trial components 200 can be trial components for a total (or anatomical) shoulder replacement (arthroplasty) or a reverse shoulder replacement. The trial components can be installable prior to installation of the permanent prosthetic components and can be used to determine fit of the joint, such as the stability of the joint, and can be used to select appropriately sized later-installed permanent prosthetic components.

In operation of some examples, a user can use button 110 to turn on or enable user interface 106. In some example, button 110 can be used to toggle between displays, units of display, sensor signals to be displayed, as well as for other functions. Once user interface 106 is enabled, in some examples, such as the example shown in FIG. 1, force F can be applied to end 104 at spoon 114 by trial components 200. Force F can be detected by a sensor within end 104, which can produce a sensor signal transmittable to user interface 106. User interface 106 can analyze the signal, using a controller, processor, and the like, and can output a value that can be visually displayed on display 112.

In the example shown in FIG. 2, display 112 can display a value of 11 on a left side of display 112, proximate left end 104. The value shown on display 112 can correspond to a signal produced by measuring force F, where the value displayed is in units of force, such as Newtons. That is, in the example of FIG. 2, display 112 indicates that force F applied to spoon 114 is 11 Newtons. Also, because a force is not applied to second end 106 (not shown in FIG. 2), display 112 shows a value of 0 Newtons proximate second end 106.

The values shown on display 112 representing forces applied to spoons 114 and 116 can be analyzed by a physician to draw conclusions regarding the operation of a shoulder. In some examples, the force values can be used to determine stability of an existing shoulder joint, trial components temporarily installed in a shoulder joint, or permanent prosthetic components installed on the shoulder joint. In some examples, a physician can make adjustments to trial components or permanent components as desired based on the analysis derived from the values. In some examples, a physician can use the analysis derived from the displayed values to select permanent components. These selection and adjustment processes can improve the fit of the permanent prosthesis and the stability of the shoulder, improving patient quality of life, improving procedural efficiency, and saving cost, in some examples.

Figure 3:
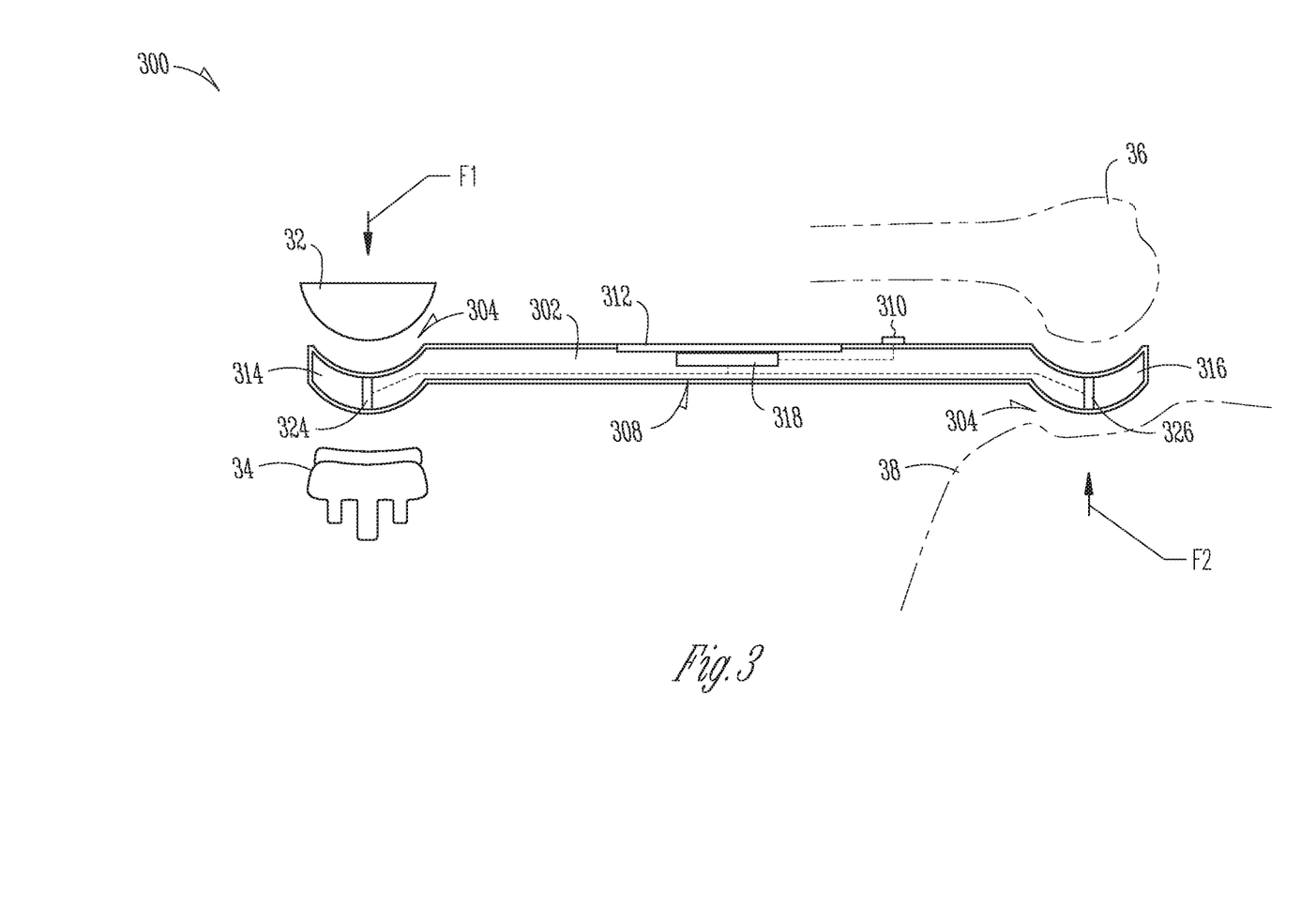
FIG. 3 illustrates a cross-sectional schematic view of a trial spoon in accordance with some examples of the present disclosure.

FIG. 3 illustrates a cross-sectional schematic view of trial spoon 300, which can include handle 302, first end 304, second end 306, and user interface 308. User interface 308 can include button 310, display 312, and printed circuit board (PCB) 318. First end 304 can include spoon 314 and sensor 324. Second end 306 can include spoon 316 and sensor 326. Also shown in FIG. 3 are convex component 32, concave component 34, humerus 36, glenoid 38, and orientation indicators Left and Right, and forces F1 and F2. FIG. 3 depicts two different scenarios (one on the left of FIG. 3 and one on the right of FIG. 3) that would not necessarily occur at the same time.

The components of FIG. 3 can be connected and can operate consistently with the components of FIGS. 1 and 2; however, FIG. 3 shows additional details of trial spoon 300 not shown in previous FIGS. and FIG. 3 illustrates some examples the interaction of trial spoon 300 with components of a shoulder.

PCB 318 can be physically coupled to display 312 and can be physically coupled to handle 302 and secured therein. PCB 318 can include a non-conductive substrate with an etched copper plate as a laminated layer that can provide the electrical connections of PCB 318, in some examples. PCB 318 can also include a processor or controller that is electrically connected to and secured by PCB 318. In some examples, PCB 318 can additionally include other electronic components enabling receipt, transmission, and analysis of signals and production of a display, such as capacitors and a communication circuit. PCB 318 can also electrically connect to button 310. In some examples, button 310 can be integral to (secured by and electrically connected to) PCB 318. PCB 318 can also electrically connect first sensor 324 and second sensor 326, as shown in FIG. 3.

First sensor 324 and second sensor 326 can be disposed within spoons 314 and 316, respectively. Each of first sensor 324 and second sensor 326 can be sensors configured to produce a signal as a function of a measured force, such as a hydraulic load cell, pneumatic load cell, strain load cell, and the like. In some examples, each of first sensor 324 and second sensor 326 can be other types of sensors, such as proximity and displacement sensors configured to produce sensor signals as a function of a sensed proximity and a sensed displacement, respectively. In some examples, first sensor 324 and second sensor 326 can wirelessly connect to PCB 318 or to an external device, such as a remote controller or processing device. Wireless connectivity can be provided through protocols such as WiFi, Bluetooth (Bluetooth LE), Near-Field Communications (NFC), and the like.

Each of spoons 314 and 316 can include a concave side and a convex side configured to engage with either a set of trial or implant components, such as convex component 32 and concave component 34, or a humerus and glenoid, such as humerus 36 and glenoid 38.

Convex component 32 and concave component 34 can be trial components or permanent implant components, such as those described above. The example shown in FIG. 3 displays convex component 32 as being a humeral trial or implant and concave component 34 as being a glenoid or scapula trial or implant, such as those commonly used in a total or anatomical arthroplasty. However, in other examples, trail spoon 300 can interface with a concave humeral component and a convex glenoid components, such as those used in a reverse shoulder arthroplasty. In some of these examples, a physician can insert trial spoon 300 to engage convex component 32 and concave component 34, where trial spoon 300 can detect forces, such as force F1 transferred between convex component 32 and concave component 34 and to spoon 314. Sensor 324 can produce a sensor signal as a function of a detected force, which can be transmitted to PCB 318. PCB 318 can process the sensor signal and output a display signal as a function of the sensor signal, where the outputted display signal is transmitted from PCB 318 to display 312. Display 312 can convert the display signal into a visual representation of the sensed force, as shown in FIG. 2.

After receiving a visual readout from display 312 of forces detected by either or both of first sensor 324 and 326, a physician can make adjustments, such as trial component selection, implant selection, bone resections, and/or soft tissue adjustments, which can improve patient quality of life and can increase procedural efficiency.

Humerus 36 and glenoid 38 can be components of a human shoulder. A concave portion of spoons 316 and 314 can be configured to interface with humerus 36 and a convex portion of spoon 316 and 314 can be configured to interface with glenoid 38. In operation of some examples, trial spoon 300 can be used to detect forces, such as force F2, transferred between humerus 36 and glenoid 38 during some procedures, such as open stabilization procedures, and partial shoulder replacements, or other procedures where a humerus and/or a glenoid is retained. In use of trial spoon 300 of these procedures, a physician can insert trial spoon 300 between humerus 36 and glenoid 38 to detect forces transferred between humerus 36 and glenoid 38. After receiving a visual readout from display 312 of forces F1 or F2 detected by either of first sensor 324 and 326, a physician can make adjustments, such as soft tissue adjustments to the shoulder joint, which can improve patient quality of life and can increase procedural efficiency.

Figure 4:
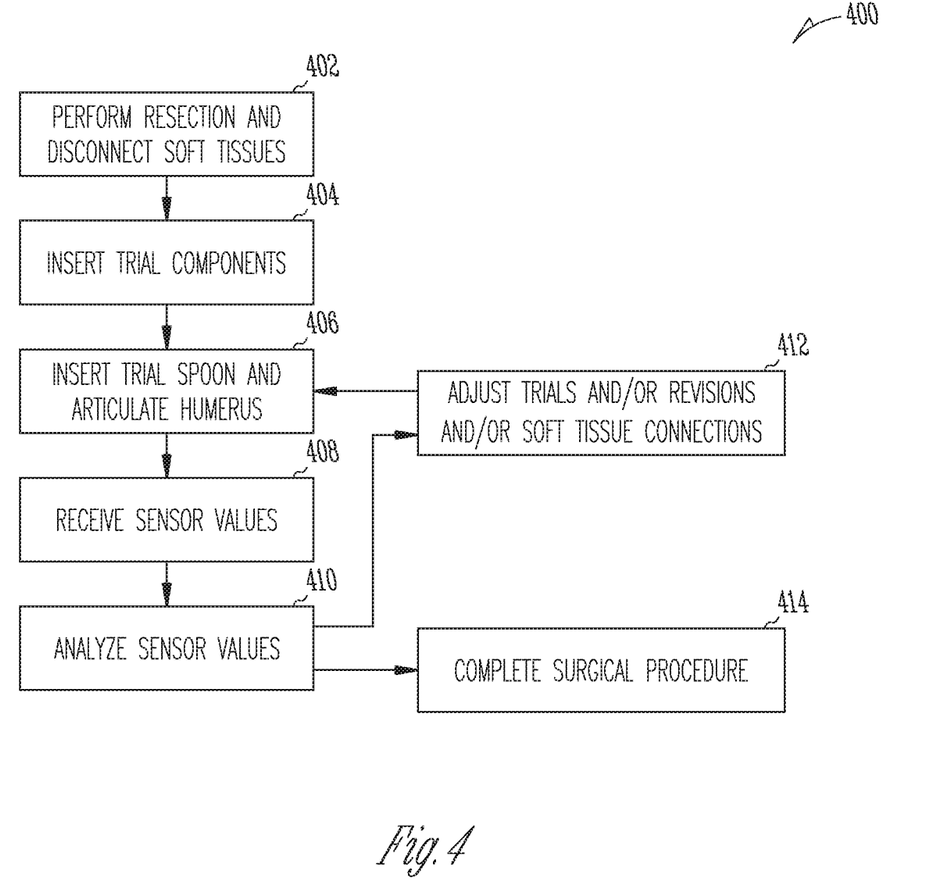
FIG. 4 illustrates a flow diagram of a method in accordance with one example of the present disclosure.

FIG. 4 illustrates method 400 of using the devices and systems described above, in accordance with at least one example of this disclosure. The steps or operations of method 400 are illustrated in a particular order for convenience and clarity; many of the discussed operations can be performed in a different sequence or in parallel without materially impacting other operations. Method 400 as discussed includes operations that may be performed by multiple different actors, devices, and/or systems. It is understood that subsets of the operations discussed in method 400 attributable to a single actor, device, or system could be considered a separate standalone process or method. At step 402, method 400 can begin with performing resections of bone and disconnections of soft tissue, such as from the humerus and the scapula. Soft tissue can also be moved and disconnected at step 402, and other preparations to the bones and soft tissues may be made. At step 404, the trial components, such as glenoid components and humeral components consistent with those described above, can be inserted into the humerus and glenoid.

Thereafter, at step 406, the physician can insert a trial spoon, such as trial spoons 100 or 300 described above, and the physician can articulate the humerus relative to the glenoid. During this process, forces may be transferred between the glenoid component and humeral component, as described above. The forces may be detected through sensors within either or both of the first and second spoons, where the sensors can produce and transmit signals as a function of the sensed forces. At step 408, the sensors signals can be received at a processor, which can analyze the signals at step 410. The analysis can be displayed through graphic images, and can enable additional analysis. Based on the analysis, the surgical procedure may be completed at step 414. If however, it is determined that the trial components, bones, or soft tissues need adjustment, these adjustments may be performed at step 412. Therefore, steps 406-412 can be repeated until it is determined that the trial components and tissue connections are adequate, at which time step 414 can be performed. Step 414 can include removing trial components, inserting permanent components, reconnecting soft tissues, and closing the incision.

This method offers the benefit of providing measurement data from a trial spoon that can be used to determine the quality of a proposed connection and adequacy of trial components or selected implant components. These methods can improve the efficiency of the procedure and can improve the longevity of the implant, by reducing potentially damaging forces from being transferred between the implant components.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. A trial tool for a human bone joint, the trial tool comprising:
a handle including a first end and a second end;
a first sensor located at the first end and configured to produce a first sensor signal based on a sensed condition of the bone joint when the first end engages an interface of the bone joint; and
a second sensor located at the second end and configured to produce a second sensor signal based on a second sensed condition of the bone joint when the second end engages the bone joint interface; and
a user interface located on the handle between the first sensor and the second sensor, the user interface configured to display a value indicative of a condition of the bone joint based on one or more of the first sensor signal and the second sensor signal.

2. The trial tool of claim 1, wherein the second sensor signal is indicative of stability of the bone joint.

3. The trial tool of claim 2, wherein the user interface is configured to display a second value based on the second sensor signal.

4. The trial tool of claim 1, wherein at least one of the first sensor and the second sensor comprises a force sensor.

5. The trial tool of claim 4, wherein the user interface is configured to display a force value based on at least one of the first sensor signal and the second sensor signal, wherein the force value is indicative of stability of the interface of the bone joint.

6. The trial tool of claim 1, the user interface comprising:
a light emitting diode (LED) display configured to display the value, wherein the value comprises a numerical.

7. The trial tool of claim 6, wherein the LED display is configured to display the value as a first numerical value representing the first sensor signal and is configured to display a second numerical value representing the second sensor signal.

8. The trial tool of claim 1, wherein the first end comprises a first size that is different from a second size of the second end.

9. The trial tool of claim 1, further comprising:
a button located between the first sensor and the second sensor and operable to change the value displayed by the user interface.

10. The trial tool of claim 9, wherein the button is operable to power on the user interface.

11. A trial system for a human bone joint, the trial system comprising:
a set of implants securable to the human bone joint; and
a trial tool comprising:
a body comprising a first end and a second end;
a spoon coupled to the first end and engageable with the set of implants, the spoon comprising a first sensor to produce a first sensor signal based on a first condition of the set of implants when the spoon engages the set of implants; and
a second spoon coupled to the second end of the body, the second spoon including a second sensor configured to produce a second sensor signal based on a second condition of the set of implants when the second spoon engages the set of implants.

12. The trial system of claim 11, wherein the first spoon comprises a first size that is different from a second size of the second spoon.

13. The trial system of claim 11, further comprising:
a user interface located on the body between the first spoon and the second spoon, the user interface configured to, based on the first sensor signal, display a value indicative of the first condition of the set of implants.

14. The trial system of claim 13, wherein the value displayed is a force value indicative of stability of the human bone joint including the set of implants.

15. The trial system of claim 13, wherein the user interface is configured to display a second value based on the second sensor signal, the displayed second value indicative of stability of the human bone joint including the set of implants.

16. A trial tool for a human bone joint, the trial tool comprising:
a handle including a first end and a second end;
a first sensor located at the first end and configured to produce a first sensor signal based on a sensed condition of the bone joint when the first end engages an interface of the bone joint; and
a second sensor located at the second end and configured to produce a second sensor signal based on a second sensed condition of the bone joint when the second end engages the bone joint interface.

17. The trial tool of claim 16, further comprising:
a user interface located on the handle between the first sensor and the second sensor, the user interface configured to display a value indicative of stability of the bone joint based on one or more of the first sensor signal and the second sensor signal.

18. The trial tool of claim 17, wherein the value is a force value based on at least one of the first sensor signal and the second sensor signal, wherein the force value is indicative of stability of a bone joint interface.

19. The trial tool of claim 17, further comprising:
a button located between the first sensor and the second sensor and operable to change a condition displayed by the user interface.

20. The trial tool of claim 19, wherein the button is operable to power on the user interface.

* * * * *